United States Patent [19]

Schittenhelm

[11] Patent Number: 5,125,012
[45] Date of Patent: Jun. 23, 1992

[54] COMPUTER TOMOGRAPHY APPARATUS

[75] Inventor: Rudolf Schittenhelm, Erlangen, Fed. Rep. of Germany

[73] Assignee: Siemens Aktiengesellschaft, Berlin and Munich, Fed. Rep. of Germany

[21] Appl. No.: 727,914

[22] Filed: Jul. 10, 1991

[30] Foreign Application Priority Data

Jul. 18, 1990 [EP] European Pat. Off. ........ 90113797.6

[51] Int. Cl.$^5$ .............................................. G21K 1/21
[52] U.S. Cl. ........................................ 378/10; 378/137
[58] Field of Search ............... 378/10, 16, 145, 134, 378/137, 143, 147, 4, 9, 26

[56] References Cited

U.S. PATENT DOCUMENTS

| | | | |
|---|---|---|---|
| 4,122,346 | 10/1978 | Enge | 378/10 |
| 4,135,095 | 1/1979 | Watanabe | 378/10 |
| 4,203,036 | 5/1980 | Tschunt | 378/10 |
| 4,274,005 | 8/1981 | Yamamura et al. | 378/137 |
| 4,866,745 | 9/1989 | Akai | 378/10 |

FOREIGN PATENT DOCUMENTS 2034149 8/1979 United Kingdom.

*Primary Examiner*—William L. Sikes
*Assistant Examiner*—Don Wong
*Attorney, Agent, or Firm*—Hill, Van Santen, Steadman & Simpson

[57] ABSTRACT

A computer tomography apparatus has an annular anode which surrounds a detector ring disposed coaxially relative thereto and having a cathode ring also disposed coaxially relative to the anode. The cathode ring has a series of cathodes which are respectively enabled step-by-step to emit electrons onto the anode so as to displace the focus. Each cathode has a deflector unit associated therewith which deflects the focus for that cathode along the circumference of the anode. One or more cathodes with associated deflection units, and an anode section, can be constructed in combination as a module. The number of focus positions is thereby increased, and the time for acquiring a set of image data is significantly reduced.

3 Claims, 4 Drawing Sheets

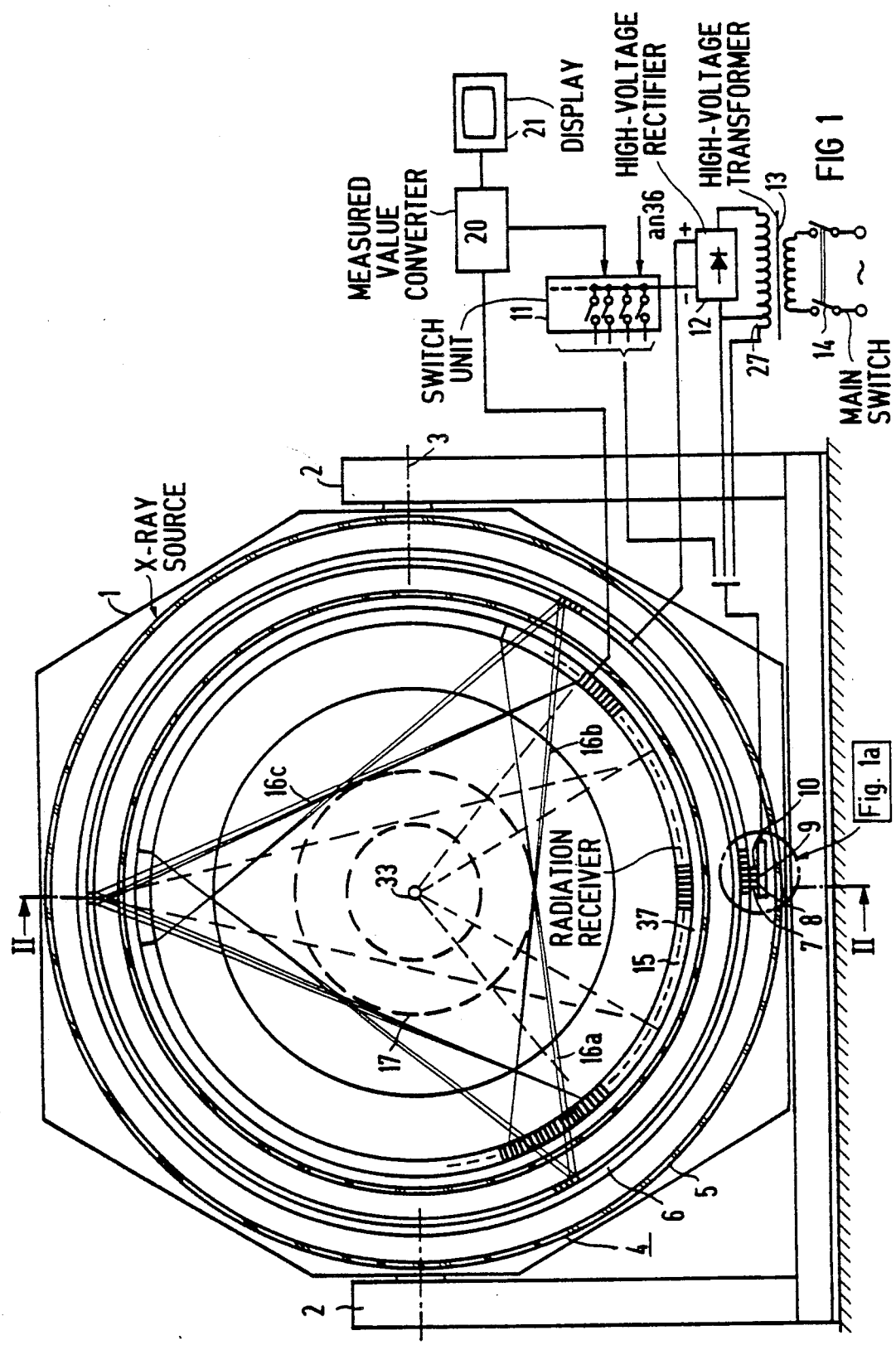

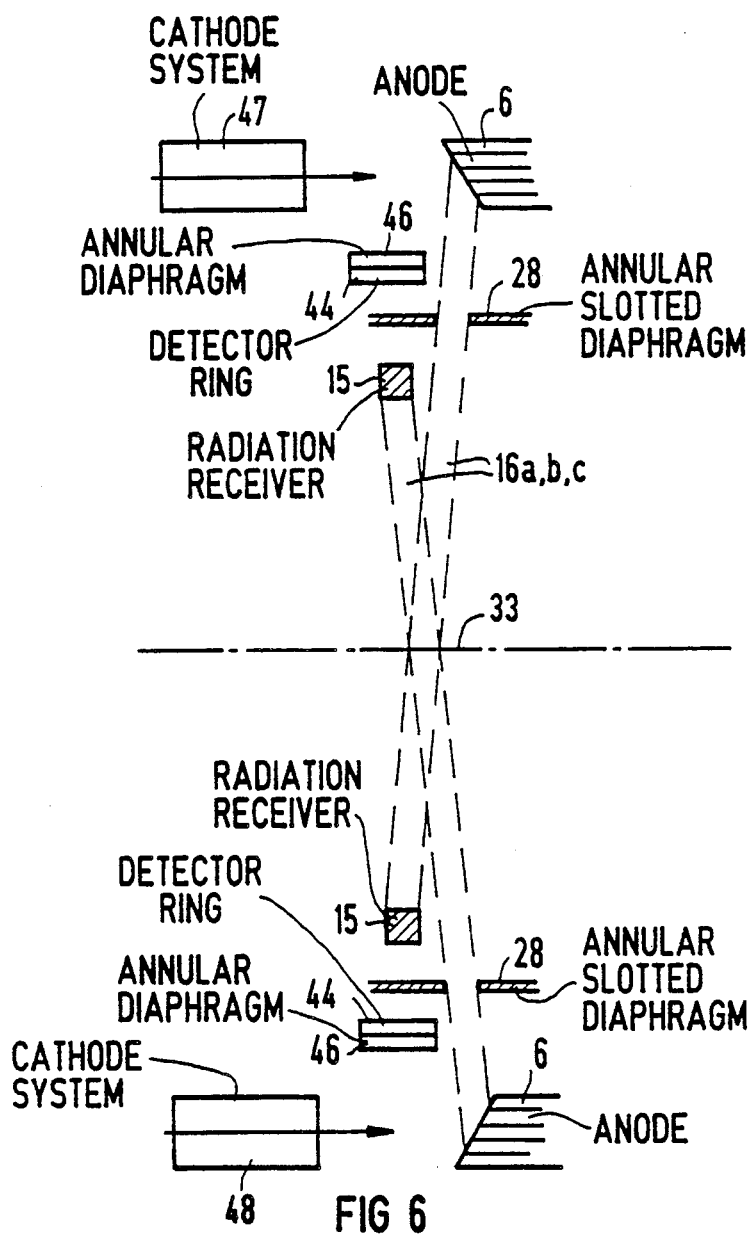
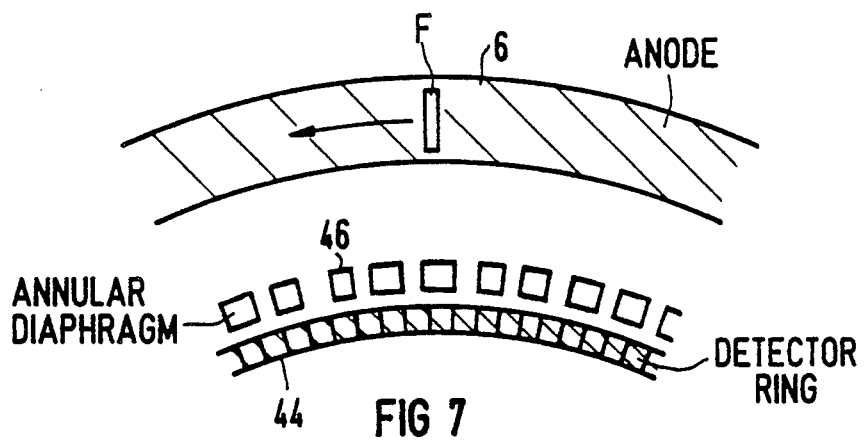

COMPUTER TOMOGRAPHY APPARATUS

BACKGROUND OF THE INVENTION

1. Field of the Invention

The present invention is directed to a computer tomography apparatus of the type having a coaxially disposed annular anode, detector ring and cathode ring.

2. Description of the Prior Art

Computer tomography systems are known in the art having an annular anode, a detector ring surrounded by the anode and a cathode ring, with the annular anode, the detector ring and the cathode ring being coaxially disposed. The cathode ring consists of a series of cathodes whose respective electron emission to the anode is enabled from cathode-to-cathode so that the focus from which x-rays are emitted by the anode is shifted step-by-step.

In a computer tomography systems of this type, the anode, the detector ring and the cathode ring are stationary while the examination subject is being scanned by a fan-shaped x-ray beam from various angles. Consequently, an extremely fast scanning of the examination subject through a total angle of 360° is possible. The image registration time, therefore, can be extremely short.

Because the individual cathodes of the cathode ring have a finite width, the number of cathodes employable in the cathode ring, and thus the number of possible focus positions, is limited. Given a center-to-center spacing of the cathodes of, for example, 4 mm, only approximately one-thousand focus positions can be accommodated on the anode having a standard circumference of approximately 4 meters. The center-to-center spacing of the cathodes cannot be arbitrarily reduced in order to increase the number of possible focus positions.

SUMMARY OF THE INVENTION

It is an object of the present invention to provide a computer tomography apparatus of the type described above wherein a higher number of focus positions, and thus a higher image quality, can be achieved.

The above object is achieved in accordance with the principles of the present invention in a tomography apparatus wherein each cathode has a deflection unit associated therewith for deflecting the focus of that cathode's emission along a circumferential direction of the anode. Accordingly, a plurality of focus positions are possible for each cathode, rather than a single focus position, by selectively deflecting the electron emission. A high number of total focus positions for all of the cathodes in combination is thus possible.

For determining the focus position when the electron emission from a particular cathode is deflected (it being necessary to know the focus position in order to reconstruct an image), a second detector ring can be provided between the anode and an annular slotted diaphragm which shapes the fan-shaped x-ray beam. This second detector ring may consist of indidual detectors, with each individual detector respectively delivering an output signal that characterizes the focus position. It is also possible to provide a diaphragm ring having openings for the passage of x-rays in front of the second detector ring, the openings being arranged and fashioned in the manner of a code. An exact identification of the focus position is then possible on the basis of the signals from the second detector ring.

DESCRIPTION OF THE DRAWINGS

FIG. 1 is an end view, partly in section of a computer tomography apparatus constructed in accordance with the principles of the present invention, with a schematic block diagram showing certain associated electronic components thereof.

FIG. 6 is a schematic illustration showing the manner of acquiring the focus position in the computer tomography apparatus of FIGS. 1 and 2.

FIG. 7 is an enlarged detail from the arrangement shown in FIG. 6.

DESCRIPTION OF THE PREFERRED EMBODIMENTS

Figure 1A:
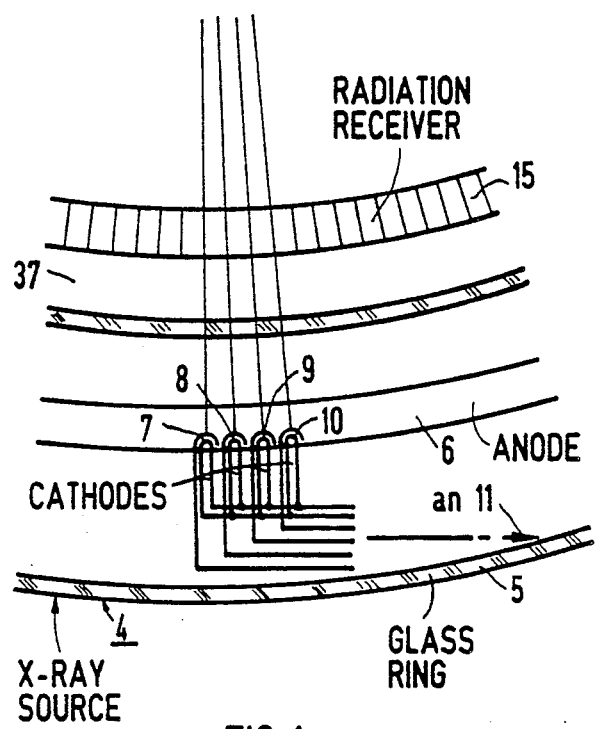
FIG. 1a is an enlarged detail of a portion of the computer tomography apparatus of FIG. 1.
Figure 2:
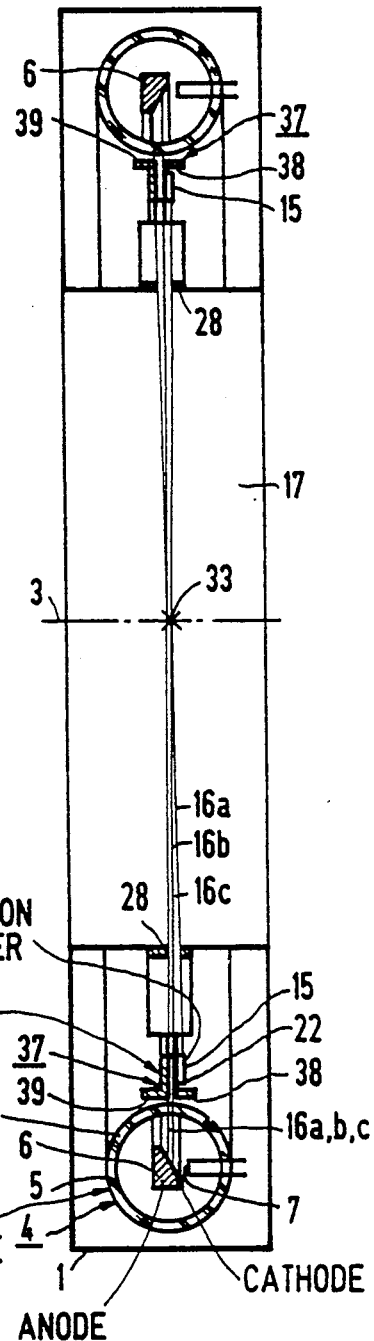
FIG. 2 is a sectional view of the computer tomography apparatus of FIG. 1 taken along line II—II.

A computer tomography apparatus constructed in accordance with the principles of the present invention is shown in various views in FIGS. 1, 1a and 2. The apparatus includes a housing 1 which is seated on two supports 2 so as to be pivotable around a horizontal axis 3. The positiion of the desired transversal slice of the examination subject can be selected by pivoting the housing 1 around the axis 3. An x-ray source 4 is arranged in the housing 1, which is formed by an evacuated tubular glass ring 5 in which an annular anode 6 is contained. The anode 6 has a plurality of cathodes 7, 8, 9, 10, . . . allocated thereto. The cathodes 7, 8, 9, 10, . . . are connected to a switch unit 11 which connects the negative pole of a high-voltage rectifier 12, fed by a high-voltage transformer 13, to the respective cathodes 7, 8, 9, 10, . . . cathode-by-cathode. The positive pole of the high-voltage rectifier 12 is connected to the anode 6. The primary winding of the high-voltage transformer 13 can be connected to the network via a main switch 14.

For a fast image registration to be possible within the shortest time, all cathodes 7, 8, 9, 10, . . . are simultaneously heated, i.e., are simultaneously connected to a filament transformer which is part of the high-voltage transformer 13, and is referenced 27 in FIG. 1. For generating x-radiation at a defined angle, the high-voltage need simply be connected to the corresponding cathode. Generation of x-rays then occurs immediately.

It is also possible to arrange a control grating between each cathode 7, 8, 9, 10, . . . and the anode 6 and to provide a switch mechanism with which each control grating can be applied to a voltage which enables that control grating for the successive activation of electron emission.

Figure 3:
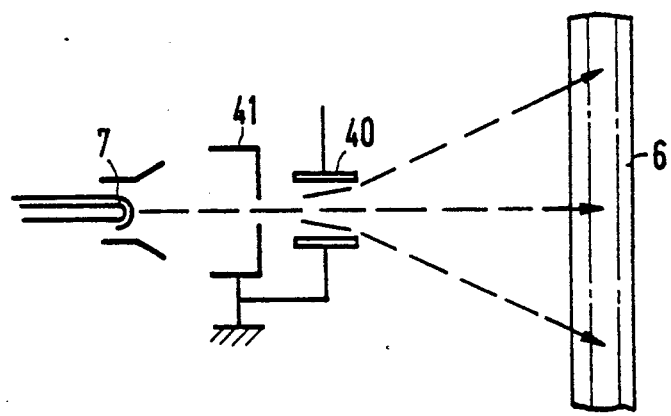
FIGS. 3, 4 and 5 are respective schematic diagrams showing various cathode systems which can be used in the tomography apparatus of FIGS. 1, 1a and 2.
Figure 4:
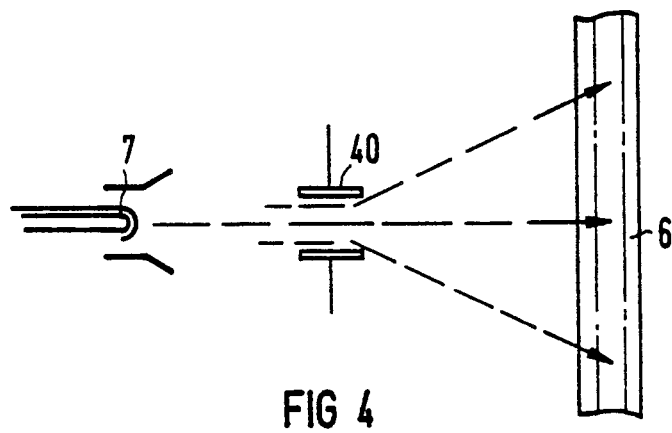

For continuously guiding the x-ray focus along the anode 6, a deflector unit 40 is shown in FIG. 3 disposed between the cathode 7 and the anode 6. The deflector unit 40 deflects the electron emission from the cathode 7 onto the anode 6. Respective deflection units operating in the same manner are also allocated to each of the other cathodes (not shown). Thus not only a focus, but also focal path is allocated to each cathode, as a result of which the total number of foci used for the image reconstruction is increased, and thus the image quality correspondingly increases. The deflection unit 40 is formed by two capacitor plates which are charged with a sawtooth voltage. A grating 41 for beam shaping may be disposed between the deflection unit 40 and the cathode 7. The grating 41 may be omitted, however, under certain circumstances, as shown in FIG. 4.

Figure 5:
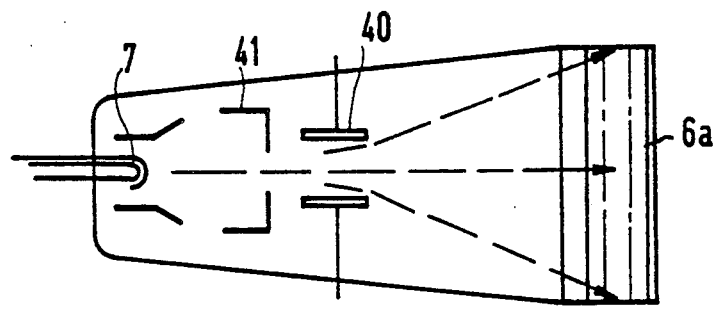

In the embodiment of FIG. 5, the cathode 7, the deflection unit 40 and an anode section 6a are combined to form a module. A plurality of such modules forms a ring disposed concentrically with respect to the center 33 of the x-ray source 4. Such modules may each contain a plurality of cathodes.

In addition to a radiation receiver 15 forming a detector ring, a second detector ring 44, consisting of a plurality of individual detectors, is provided for acquiring the focus position for each cathode. The detector ring 44 is disposed between the anode 6 and an annular slotted diaphragm 28, which shapes the fan-shaped x-ray beams 16a, 16b and 16c. These components are shown in FIG. 6 as well as an annular diaphragm 46 disposed in front of the second detector ring 44 in the direction of radiation propagation. FIG. 6 also includes two schematically indicated cathode systems 47 and 48.

As can be seen in FIG. 6, the x-rays emanating from the anode 6 incident on the detector elements of the detector ring 44 through the diaphragm 46, i.e., through slots provided therein. The output signals obtained from the detector ring 44 can thus be used to determine the respective focus position F (FIG. 7).

As also shown in FIG. 7, a precise acquisition of the focus position is possible if the slots of the diaphragm 46 are non-uniform, which achieves a coding of the output signals of the detector elements of the detector ring 44.

The x-ray source 4 concentrically surrounds the radiation receiver 15, which is also in the form of an annular ring, and consists of a series of individual detectors. The number of such individual detectors depends on the desired number of measured values. The diaphragm arrangement 28 is provided for gating the fan-shaped x-ray beam 16a, 16b and 16c.

The exemplary embodiment of FIG. 1 provides three x-ray beams 16a, 16b and 16c offset relative to each other, so that a very rapid scanning of the examination subject is possible. An individual x-ray beam thus has to sweep only an angle of approximately 120°. Dependent on the scattered radiation correction, however, it is possible within the context of the present invention to use only two x-ray beams or only one x-ray beam. In these respective cases, an x-ray beam must sweep an angle of 180° or 360°. As a result of the electronic change in the focus position, an extremely rapid scanning is still possible in these systems as well.

The switch unit 11 is constructed so that a plurality of x-ray beams, namely three x-ray beams 16a, 16b and 16c, simultaneously penetrate the patient from different directions, and migrate in identical steps synchronized with each other. The central rays of the x-ray beams 16a, 16b, and 16c are thereby offset by 120° relative to each other.

The radiation receiver 15 is laterally arranged at an annular slit diaphragm 37 which limits the x-ray beams 16a, 16b and 16c perpendicular to the sectional plane, and has projections 38 and 39 for shielding the x-rays directed onto the examination subject.

The housing 1 has a central opening 17 into which a patient support and the patient can be introduced.

The radiation receiver 15 is connected to a measured value converter 20 which calculates an image of the transirradiated transversal slice of the examination subject from the measured values, and reproduces this image on a display 21.

The x-ray beams 16a, 16b and 16c and the radiation receiver 15 are aligned with respect to each other so that, as seen in the direction of radiation propagation, the x-ray beams first laterally pass by the radiation receiver 15 at the location 22 and are incident on the radiation receiver 15 after they have transirradiated the examination subject.

For examining a subject, i.e., for registering a tomogram, three switches of the switch unit 11 are first closed. As a result, high-voltage is applied between the anode and three cathodes, and the x-ray beams 16a, 16b and 16c are emitted, for example, in the directions shown in FIG. 1. After the measured value converter 20 has processed the measured values of the radiation receiver 15, it forwards a signal to the switch unit 11 to open these switches, and to close a next combination of three switches. The symmetry axis of the x-ray beam therefore migrates by, for example, 0.1° in a clockwise direction. After the measured value converter 20 has again sampled the measured values of the radiation receiver 15, it forwards a signal to the switch unit 11 to open the closed switches and to close a further combination of three switches. The symmetry axis of the x-ray beam thus migrates another 0.1°. The step-by-step rotation of the x-ray beam is repeated until each x-ray beam has swept a predetermined angular range of, for example, 120°. The image registration is then over, and the calculated cross-sectional image can be reproduced on the display 21.

It can be seen in FIG. 1 that the x-ray beams 16a, 16b and 16c are fan-shaped and are of such a size in the sectional plane that the entire patient is simultaneously transirradiated. The extent of the x-ray beams perpendicular to the sectional plane is approximately the same as the slice thickness.

Although modifications and changes may be suggested by those skilled in the art, it is the intention of the inventor to embody within the patent warranted hereon all changes and modifications as reasonably and properly come within the scope of his contribution to the art.

I claim as my invention:

1. A computer tomography apparatus comprising:
   an annular anode;
   a radiation detector ring surrounded by said annular anode and disposed coaxially relative to said annular anode;
   a cathode ring disposed coaxially relative to said annular anode and having a plurality of individually energizable cathodes, each cathode generating a respective electron emission onto said anode;
   means for energizing said cathodes cathode-by-cathode to migrate a focus associated with the electron emission of a cathode step-by-step on said anode; and
   deflection means respectively associated with each cathode for acting on the electron emission of the associated cathode to displace the focus of the electron emission along a circumferential direction of said annular anode.

2. A computer tomography apparatus as claimed in claim 1 wherein at least one cathode, a deflection means allocated to said at least one cathode, and a section of said annular anode are combined as a module.

3. A computer tomography apparatus as claimed in claim 1 further comprising:
   an annular slotted diaphragm which shapes a fan-shaped x-ray beam from each focus position; and
   a second detector ring disposed between said annular anode and said annular slotted diaphragm for identifying the position of a focus on said annular anode.

* * * * *